United States Patent [19]

Keane et al.

[11] Patent Number: 5,270,341

[45] Date of Patent: Dec. 14, 1993

[54] METHOD OF TREATMENT OR PROPHYLAXIS OF DEPRESSION AND STRESS

[75] Inventors: Peter-Eugène Keane, Roquettes, France; Alberto Bianchetti, Milan, Italy; Jacques Simiand, Muret, France; Tiziano Croci, Milan, Italy

[73] Assignee: Elf Sanofi, Paris, France

[21] Appl. No.: 804,580

[22] Filed: Dec. 4, 1991

[30] Foreign Application Priority Data

Dec. 4, 1990 [FR] France ................... 90 15171

[51] Int. Cl.$^5$ .................... A61K 31/24; A61K 31/195
[52] U.S. Cl. ..................................... 514/510; 514/567; 514/539
[58] Field of Search ......... 514/539, 567, 510

[56] References Cited

U.S. PATENT DOCUMENTS 4,707,497 11/1987 Cecchi et al. ................. 514/647
4,927,955 5/1990 Boigegrain et al. ............ 560/45

FOREIGN PATENT DOCUMENTS 303545 2/1989 European Pat. Off. .
0403360 12/1990 European Pat. Off. .
2643076 8/1990 France .

Primary Examiner—Frederick E. Waddell
Assistant Examiner—Raymond J. Henley, III
Attorney, Agent, or Firm—Foley & Lardner

[57] ABSTRACT

The invention concerns a method of treatment and prophylaxis of depression and stress by means of a phenylethanolaminotetralin of formula (I)

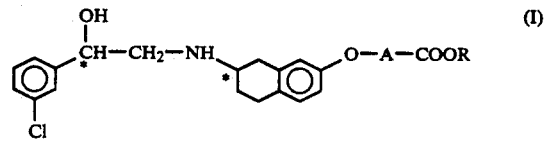

wherein A is a ($C_1$-$C_4$)alkylene radical and R represents a hydrogen atom or a ($C_1$-$C_4$)alkyl group, or a pharmaceutically acceptable salts thereof.

7 Claims, No Drawings

METHOD OF TREATMENT OR PROPHYLAXIS OF DEPRESSION AND STRESS

The present invention concerns the use of some phenylethanolaminotetralins for the treatment or prophylaxis of depression and stress.

More particularly a first object of the present invention is a method of treating or preventing depression and stress which comprises administering to a mammal in need thereof a therapeutically or prophylactically effective amount of at least one phenylethanolaminotetralin of general formula (I)

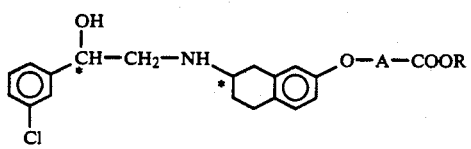

wherein
A represents a $(C_1-C_4)$alkylene radical and
R is hydrogen or a $(C_1-C_4)$alkyl group,
or one of its pharmaceutically acceptable salts.

The compounds of formula (I) are already known in the prior-art as intestinal spasmolytics acting through a mechanism of selective stimulation of $\beta$ atypical receptors (non $\beta_1$ non $\beta_2$) which are present in the intestine. Their preparation and their characteristics have been described in particular in EP-A-211,721, EP-A-303,545, EP-A-303,546 and EP-A-383,686.

About fifteen years ago, a sedative effect was clearly demonstrated for the classical $\beta$-adrenergic stimulants (A. Ksiazek et al. J. Pharmacol. Pharm., 26, 287–295, 1974) and the results of more recent studies also indicated antidepressant efficacy for some $\beta_2$-adrenergic stimulants, such as clenbuterol and salbutamol, which might be related to their central $\beta$-adrenergic stimulating activity.

In spite of these promising pharmacological results, the concurrent cardiovascular side-effects of these classical $\beta$-adrenergic stimulants make their use in therapy not recommendable.

It has now been found that the compounds of formula (I) which possess a stimulating activity on atypical $\beta$-adrenoceptors, are almost completely inactive on $\beta_1$-adrenoceptors and have no activity or only a slight activity on $\beta_2$-adrenoceptors, are therapeutically very interesting as antidepressant agents, as they have an antidepressant activity at least comparable to that of the above mentioned potent classical $\beta_2$-agonists and in the meantime are devoid of the unacceptable side-effects (mainly tachycardia) observed with these last compounds.

The antidepressant properties of the compounds of formula (I) have been studied by means of a set of tests in animals conventionally employed in pharmacology and generally considered predictive of antidepressant activity in man (P. Simon, Thérapie, 1973, 28, 209–223). More particularly the compounds of formula (I) have been tested in mice in comparison with clenbuterol and salbutamol in the following four tests:

Antagonism of apomorphine-induced hypothermia
Antagonism of reserpine-induced hypothermia
Antagonism of oxotremorine-induced hypothermia
Potentiation of yohimbine toxicity Possible behavioural or locomotor activity modifications following administration of increasing doses of test compounds have also been evaluated.

The compounds of formula (I) share some common effects with the classical $\beta$-adrenergic agonists employed as reference compounds e.g. clenbuterol and salbutamol: antagonism to the hypothermias induced in mice by reserpine, oxotremorine, or a high dose of apomorphine, and potentiation of yohimbine toxicity. Unlike clenbuterol and salbutamol, the compounds of formula (I), however, do not elicit any sedation or any decrease of spontaneous locomotor activity in mice. These tests have been carried out as follows:

Antagonism of apomorphine-induced hypothermia
(A. J. Puech et al. Psychopharmacology, 75(1), 84–91, 1981)

Male CD1 mice (Charles River-France) weighing 22–25 g were used in the test. The mice were housed individually in transparent plastic cages. The compounds of formula (I) as well as the reference compounds were suspended in 1% aqueous carboxymethylcellulose and administered intraperitoneally (10 ml/kg; 6 mice per dose). Control animals received the vehicle only.

Rectal temperature was measured using a probe carrying a thermoelectric couple (connected to a galvanometer) inserted to a constant depth.

The compounds to be tested as well as the vehicle were administered 30 minutes after basal rectal temperature was measured and 30 minutes later apomorphine (16 mg/kg) was administered subcutaneously. Rectal temperature was measured again 30 minutes after the administration of apomorphine.

The results have been expressed as average rectal temperature of each group, by evaluating the significant differences in temperature between treated and control mice by Student's t test, and used for calculating the M.A.D., i.e. the minimal active dose. The results are presented in following Table I

TABLE I

| COMPOUND | Antagonism of the hypothermia induced by apomorphine (16 mg/kg s.c.) M.A.D. mg/kg i.p. |
|---|---|
| N-[(2S)7-ethoxycarbonylmethoxy-1,2,3,4-tetrahydronaphth-2-yl]-(2R)-2-hydroxy-2-(3-chlorophenyl)ethanamine hydrochloride (Compound A) | 0.1 (0.3 p.o.) |
| N-[(2R)7-ethoxycarbonylmethoxy-1,2,3,4-tetrahydronaphth-2-yl]-(2R)-2-hydroxy-2-(3-chlorophenyl)ethanamine hydrochloride (Compound B) | 0.1 |
| N-[(2S)7-ethoxycarbonylmethoxy-1,2,3,4-tetrahydronaphth-2-yl]-(2S)-2-hydroxy-2-(3-chlorophenyl)ethanamine hydrochloride (Compound C) | 1 |
| N-[(2S)7-(2-ethoxycarbonyl-propan-2-yloxy)-1,2,3,4-tetrahydronaphth-2-yl]-(2R)-2-hydroxy-2-(3-chlorophenyl)ethanamine hydrochloride (Compound D) | 0.3 |
| N-[(2R)7-(2-ethoxycarbonyl-propan-2-yloxy)-1,2,3,4-tetrahydronaphth-2-yl]-(2R)-2-hydroxy-2-(3-chlorophenyl)ethanamine hydrochloride (Compound E) | 0.3 |
| Clenbuterol | 0.03 |
| Salbutamol | 1 |

Motor activity

While clebuterol and salbutamol reduce motor activity in mice, up to 35% of the controls with 0.03 mg/kg of clenbuterol and up to 62% of the controls with 1 mg/kg of salbutamol, the compounds of formula (I) listed in Table I above, at the doses indicated therein, almost do not affect motor activity, Compound A being completely inactive in this respect even at the dose of 10 mg/kg i.p.

Antagonism of the reserpine-induced hypothermia

The compounds of formula (I) as well as the reference compounds were administered 4 hours after reserpine (2.5 mg/kg i.p.). Rectal temperature was measured 90 minutes after the administration of the compounds to be tested. The results obtained with Compound A, as a representative compound of formula (I), are summarized in Table II below

TABLE II

| COMPOUND | Dose mg/kg i.p. (groups of 6 to 10 mice per dose) | Rectal temperature °C. (±E.S.M.) 1 h 30 after the administration of the test compounds; 5 h 30 after the injection of reserpine (2.5 mg/kg i.p.) | M.A.D. mg/kg i.p. |
|---|---|---|---|
| Compound A | 0 | 28.9 ± 0.3 | 0.1 (1 p.o.) |
| | 0.1 | 30.3 ± 0.4* | |
| | 0.3 | 30.7 ± 0.3** | |
| | 1 | 31.4 ± 0.2*** | |
| Clenbuterol | 0 | 32.8 ± 0.3 | 0.03 |
| | 0.03 | 34.0 ± 0.4* | |
| | 0.1 | 35.2 ± 0.4*** | |
| | 0.3 | 34.5 ± 0.3*** | |
| Salbutamol | 0 | 29.9 ± 0.6 | 3 |
| | 1 | 30.5 ± 0.9 | |
| | 3 | 32.6 ± 0.4** | |
| | 10 | 32.0 ± 0.7* | |

*P < 0.05
**P < 0.01
***P < 0.001

Antagonism of the oxotremorine-induced hypothermia

The test compounds were administered 30 minutes before oxotremorine (0.4 mg/kg i.p.). Rectal temperature was measured 30 minutes after the administration of oxotremorine. The oxotremorine-induced hypothermia was antagonised, at least partially, by the compounds of formula (I) as well as by the reference compounds With Compound A, whose activity in this test has been investigated more deeply, it was shown that the antagonism regularly increases with the dose.

Potentiation of yohimbine toxicity

Yohimbine administration (30 mg/kg s.c.) generally causes the death of one out of ten mice. Potentiation of this toxicity by the test compounds was evaluated by administering the test compounds intraperitoneally 30 minutes before yohimbine and calculating the number of deaths in the 24 hours following yohimbine s.c. injection. The compounds of formula (I) which were submitted to this test showed a clear potentiation of yohimbine toxicity comparable to that of the reference compounds.

In addition to the antidepressant activity, the compounds of formula (I) are also endowed with a remarkable anti-stress activity.

Several recent studies have shown that stress may have a great influence on a number of physiological processes. It is widely known for instance that exposure to stress generating conditions generally brings about reduced immunological functions, intestinal motility troubles, etc.. The existence of such a link between stress and some pathological conditions, indicated herein as "stress-induced" conditions, increases the therapeutical interest of the compounds of formula (I) which may therefore be employed in the treatment of depression as well as in the treatment of stress and therefore of stress-induced pathological conditions.

For the evaluation of the anti-stress activity of the compounds of formula (I), male CD(BR)SD rats (Charles River-Italy), weighing 220-250 g, were employed and acutely stressed by completely restraining them, flat on their chests, on small boards by means of adhesive tape. Three pairs of electrodes were chronically implanted on the animal colon (proximal, distal, and transverse colon) and the wires were exteriorised in the scapular region and connected to an electroencephalograph for recording of myoelectrical activity. The parameter used to evaluate this activity was the number of long-duration spike bursts (LBS) per minute. Almost immediately upon restraint, the electromyographic response of the colon remarkably increases with respect to the unrestrained controls; the faecal excretion also increases.

These effects remain nearly stable during the first hour and begin to decrease during the second. Administration of a compound of formula (I) just before restraint protects the animals against the stress and reduces both electromyographic response and faecal excretion with respect to the restrained controls.

Said protective effect against the stress is obtained also when the compounds of formula (I) are administered intracranially at very low doses which definitely exclude any peripheral effect on colon. The central anti-stress effects elicited by the compounds of formula (I) are similar to those obtained with benzodiazepines and in particular with diazepam.

The results obtained with Compound A, a representative compound of formula (I), are summarized in following Tables III and IV

TABLE III

Effects of Compound A and diazepam on stress-stimulated colon myoelectrographic activity in rats

| COMPOUND | DOSE mg/kg | Colon myoelectrographic activity (LSB/min) during the first hour of stress | | |
|---|---|---|---|---|
| | | Proximal | Transverse | Distal |
| Unrestrained controls | — | 1.75 ± 0.06 | 1.10 ± 0.15 | 0.85 ± 0.12 |
| Restrained controls | — | 2.41 ± 0.14** | 1.75 ± 0.37* | 1.42 ± 0.25* |
| Compound A | 0.2 (p.o.) | 1.63 ± 0.11˚ | 1.20 ± 0.15 | 0.67 ± 0.27˚ |
| | 0.5 (p.o.) | 1.07 ± 0.14˚˚* | 1.28 ± 0.25 | 0.63 ± 0.12˚ |
| | 2 (p.o.) | 0.76 ± 0.12˚˚** | 1.16 ± 0.22 | 0.66 ± 0.17 |
| | 0.003 (i.c.v.) | 2.07 ± 0.09 | 1.25 ± 0.18 | 0.71 ± 0.15˚ |
| Diazepam | 2 (s.c.) | 1.64 ± 0.12 | 0.99 ± 0.08 | 0.52 ± 0.07˚˚ |

*P < 0.05 v. unrestrained controls
**P < 0.01 v. unrestrained controls
˚P < 0.05 v. restrained controls
˚˚P < 0.01 v. restrained controls

TABLE IV

| COMPOUND | DOSE mg/kg | Faecal excretion during the first hour of stress | |
|---|---|---|---|
| | | Faeces - Dry weight (g ± S.E.) | % inhibition over restrained controls |
| Unrestrained controls | — | 0 ± 0 | — |

TABLE IV-continued

| COM-POUND | DOSE mg/kg | Faecal excretion during the first hour of stress | |
|---|---|---|---|
| | | Faeces - Dry weight (g ± S.E.) | % inhibition over restrained controls |
| Restrained controls | — | 1.24 ± 0.05 | — |
| Compound A | 0.2 (p.o.) | 0.80 ± 0.06** | 35 |
| | 2 (p.o.) | 0.41 ± 0.07** | 67 |
| Diazepam | 2 (s.c.) | 0.51 ± 0.07** | 59 |

**P < 0.01 v. restrained controls

Furthermore, the compounds of formula (I) and their pharmaceutically acceptable salts have a very low toxicity which is compatible with their use as drugs.

In view of the above a first object of the present invention is therefore a method of treatment or prophylaxis of depression and stress by administering a therapeutically or prophylactically effective dose of at least one compound of formula (I) or of a pharmaceutically acceptable salt thereof.

A preferred object of the present invention is a method of treatment or prophylaxis of depression which comprises administering to a mammal in need thereof an antidepressant effective dose of at least one compound of formula (I) or a pharmaceutically acceptable salt thereof.

Another preferred object of the present invention is a method of treatment or prophylaxis of stress and stress-induced pathological conditions, particularly those associated with intestinal motility troubles which comprises administering to a mammal in need thereof an anti-stress effective dose of at least one compound of formula (I) or a pharmaceutically acceptable salt thereof.

As used herein, the term pharmaceutically acceptable salts includes the acid addition salts of pharmaceutically acceptable mineral or organic acids as well as the salts of the compounds of formula (I) wherein R is hydrogen with mineral bases, preferably those with alkali metals such as sodium or potassium, or with pharmaceutically acceptable organic bases.

Among the acids which can be employed for the salification of the free base, there may be cited i.a. hydrochloric acid, hydrobromic acid, acetic acid, formic acid, propionic acid, oxalic acid, fumaric acid, maleic acid, succinic acid, benzoic acid, cinnamic acid, mandelic acid, citric acid, malic acid, tartaric acid, aspartic acid, glutamic acid, methanesulfonic acid, p-toluenesulfonic acid, and the like. The hydrochloride is anyway the preferred acid addition salt according to the present invention.

In the above formula (I), the two asymmetric carbons are marked by an asterisk. All the compounds of formula (I) may therefore exist in at least four isomeric forms [(R,R), (R,S), (S,S), and (S,R)].

The optically pure isomers, as well any mixture of two, three, or all four isomers, in any proportion, may be employed for the methods of treatment and prophylaxis according to the present invention.

An additional chiral center may be present in the radical A. Analogously, the stereoisomers derived from such additional chiral center and their mixtures may be employed according to the present invention. It is however understood that, as it often happens when dealing with pharmaceutically active compounds possessing one or more chiral centers, the different stereoisomers may have different activity levels. If desired, the person skilled in the art may, on the basis of the indications given in the present application and his own experience, choose from the different stereoisomers of formula (I) the compound or compounds which are therapeutically most interesting.

Anyway, the compounds of formula (I) wherein the carbon atom linked to the hydroxy group has absolute configuration (R), are generally more interesting and the use of at least one compound of formula (I) wherein the carbon atom linked to the hydroxy group has absolute configuration (R) in a method of treating depression and stress represents a preferred embodiment of the present invention.

A preferred group of compounds of formula (I) for the method according to the present invention comprises those compounds of formula (I) wherein A is methylene or isopropylidene and the carbon atom linked to the hydroxy group has absolute configuration (R).

Even more preferred compounds are the compounds of formula (I) wherein A is methylene and R is methyl or ethyl.

For the treatment or prophylaxis of depression and stress the compounds of formula (I) may be administered orally, sublingually, transdermally, rectally, subcutaneously, intramuscularly, or intravenously.

The amount of active principle to be administered will depend, as usually, on the nature and severity of the pathological conditions to be treated as well as on the weight of the patient and the administration route.

In human beings the daily dosage typically varies between 0.01 and 30 mg/kg of body weight, and preferably between 0.01 and 10 mg/kg of body weight. Said daily dosage is generally subdivided in 2, 3, or 4 administrations.

Preferably, for the treatment or prophylaxis of depression and stress, the active principles (the compounds of formula (I) and their pharmaceutically acceptable salts) are formulated in unit dosage forms containing from 0.1 to 400 mg and more preferably from 0.5 to 100 mg of active principle in admixture with a pharmaceutical vehicle. Unit dosage forms suitable for oral administration include tablets, capsules, powders, granules, and solutions or suspensions for oral use.

When a solid composition is prepared in the form of tablets, the main active ingredient is mixed with a pharmaceutical carrier such as gelatine, starch, lactose, magnesium stearate, talc, arabic gum, and the like. The tablets may be coated with sucrose or other appropriate materials or they may be treated so that their activity is extended or delayed and they continuously release a predetermined amount of active ingredient.

A preparation in the form of capsules is obtained by mixing the active ingredient with a diluent and filling the obtained mixture in soft or hard capsules.

A preparation in the form of a syrup or elixir or for the administration in drops, may contain the active ingredient jointly with a sweetening agent, possibly acaloric, methylparaben and propylparaben as antiseptics, a flavoring agent and an appropriate dye.

Water-dispersible powders or granules may contain the active principle mixed with dispersing agents, wetting agents or suspending agents such as polyvinylpyrrolidone and the like, and with sweetening or flavouring agents as well.

For rectal administration, suppositories can be employed which are prepared with vehicles melting at rectal temperature, such as cocoa butter or polyethyleneglycols.

For sublingual administration microtablets or microcapsules can be prepared which, placed under the tongue, will rapidly dissolve. These compositions will generally contain the active ingredient in admixture with wetting and/or dispersing agents and optionally with absorption enhancers.

For transdermal administration, the use of polymeric diffusion matrices for the continuous and preferably sustained release of the active principle can be devised as well as the use of the active principle as a microemulsion with excipients adapted for contact with the skin.

For parenteral administration, aqueous suspensions, isotonic saline solutions, or sterile injectable solutions are used, which contain pharmaceutically compatible dispersing and/or wetting agents, for example propyleneglycol or butyleneglycol.

The active principle of formula (I) may also be formulated in the form of microcapsules, possibly with one or more carriers or additives.

The active principle of formula (I) may be administered as the free base or a pharmaceutically acceptable salt thereof, as such or complexed with a cyclodextrine, or even in admixture with or associated to other active principles.

By way of example, suitable pharmaceutical compositions may be prepared as follows:

Tablets containing Compound A as the active ingredient and having the following composition

| Compound A | 5 mg |
| --- | --- |
| Microcrystalline cellulose | 40 mg |
| Dried corn starch | 40 mg |
| Lactose | 100 mg |
| Magnesium stearate | 5 mg | are prepared by grinding the active ingredient to a particle size of 0.4 mm, passing it through a sieve with 0.4 mm openings, mixing the obtained ground active principle with the other ingredients and compressing the mixture to obtain tablets. Analogously, tablets containing 10 mg of active principle can be obtained.

By operating essentially as described above but using Compound D as the active principle, tablets with the following composition are prepared

| Compound D | 50.0 mg |
| --- | --- |
| Dried corn starch | 100.0 mg |
| Lactose | 95.0 mg |
| Talc | 4.5 mg |
| Magnesium stearate | 0.5 mg |

10,000 capsules containing 20 mg each of active principle are prepared starting from the following ingredients: Compound A (200 g), microcrystalline cellulose (990 g), amorphous silica (10 g). The above ingredients are mixed together and then filled into hard gelatin capsules.

An aqueous sterile solution suitable for parenteral administration, as a mono-dose form, has the following composition:

| Compound A | 5 mg |
| --- | --- |
| Sodium chloride | 1 mg |
| Distilled water q.s.p. | 2 ml |

We claim:

1. A method of treatment or prophylaxis of depression which comprises administering to a mammal in need thereof a therapeutically or prophylactically effective amount of at least one compound of formula (I)

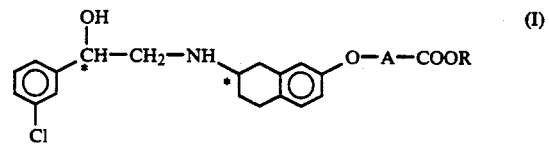

wherein A represents a $(C_1-C_4)$alkylene group and R stands for a hydrogen atom or a $(C_1-C_4)$alkyl group, or of a pharmaceutically acceptable salt thereof.

2. A method according to claim 1 wherein A represents a methylene or isopropylidene group.

3. A method according to claim 1 wherein the carbon atom linked to the hydroxy group has absolute configuration (R).

4. A method according to claim 1 wherein R is methyl or ethyl.

5. The method according to claim 4 wherein said compound of formula (I) is N-[(2S) 7-ethoxycarbonylmethoxy-1,2,3,4-tetrahydronaphth-2-yl]-(2R)-2-hydroxy-2-(3-chlorophenyl)ethanamine or a pharmaceutically acceptable salt thereof.

6. A method according to claim 1 wherein the compound of formula (I) or a pharmaceutically acceptable salt thereof is administered in a daily dosage of from 0.01 to 30 mg/kg.

7. A method according to claim 6 wherein said daily dosage is comprised between 0.01 and 10 mg/kg.

* * * * *